(12) United States Patent
Le et al.

(10) Patent No.: US 7,865,235 B2
(45) Date of Patent: *Jan. 4, 2011

(54) METHOD AND SYSTEM FOR DETECTING AND CLASSIFYING THE MENTAL STATE OF A SUBJECT

(76) Inventors: Tan Thi Thai Le, Suite 12, Jones Bay Wharf 19-21, 26-32 Pirrama Road, Pyrmont, New South Wales 2009 (AU); Nam Hoai Do, Suite 12, Jones Bay Wharf 19-21, 26-32 Pirrama Road, Pyrmont, New South Wales 2009 (AU); William Andrew King, Suite 12, Jones Bay Wharf 19-21, 26-32 Pirrama Road, Pyrmont, New South Wales 2009 (AU); Hai Ha Pham, Suite 12, Jones Bay Wharf 19-21, 26-32 Pirrama Road, Pyrmont, New South Wales 2009 (AU); Johnson Thie, Suite 12, Jones Bay Wharf 19-21, 26-32 Pirrama Road, Pyrmont, New South Wales 2009 (AU); Emir Delic, Suite 12, Jones Bay Wharf 19-21, 26-32 Pirrama Road, Pyrmont, New South Wales 2009 (AU)

( * ) Notice: Subject to any disclaimer, the term of this patent is extended or adjusted under 35 U.S.C. 154(b) by 271 days.

This patent is subject to a terminal disclaimer.

(21) Appl. No.: 11/225,835

(22) Filed: Sep. 12, 2005

(65) Prior Publication Data
US 2007/0060831 A1 Mar. 15, 2007

(51) Int. Cl.
*A61B 5/04* (2006.01)
(52) U.S. Cl. .................................................... 600/544
(58) Field of Classification Search ................... 600/545
See application file for complete search history.

(56) References Cited

U.S. PATENT DOCUMENTS 5,601,090 A * 2/1997 Musha ....................... 600/544

(Continued)

FOREIGN PATENT DOCUMENTS

EP 1 139 240 A2 10/2001

(Continued)

OTHER PUBLICATIONS

Allanson, Jennifer et al., 'A research agenda for physiological computing', Interacting with Computers, Butterworth-Heinemann, GB, vol. 16, No. 5, Oct. 2004, pp. 857-878, XP004638961 ISSN: 0953-5438.

(Continued)

*Primary Examiner*—Patricia C Mallari

(57) ABSTRACT

A method of detecting and classifying mental states, comprising the steps of: detecting bio-signals from one or more than one bio-signal detector; transforming the bio-signals into one or more than one different representations; detecting values of one or more than one property of the transformed bio-signal representations; and applying one or more than one mental state detection algorithm to the detected properties in order to classify whether the bio-signals indicate the presence of a predetermined response by a subject.

17 Claims, 8 Drawing Sheets

U.S. PATENT DOCUMENTS

| | | | |
|---|---|---|---|
| 5,724,987 A | 3/1998 | Gevins et al. | 600/544 |
| 5,740,812 A | 4/1998 | Cowan | |
| 6,021,346 A * | 2/2000 | Ryu et al. | 600/544 |
| 6,097,981 A | 8/2000 | Freer | 600/545 |
| 6,129,681 A | 10/2000 | Kuroda et al. | 600/544 |
| 6,292,688 B1 | 9/2001 | Patton | |
| 6,349,231 B1 | 2/2002 | Musha | 600/544 |
| 6,422,999 B1 | 7/2002 | Hill | |
| 2002/0188217 A1 | 12/2002 | Farwell | |
| 2003/0032890 A1 | 2/2003 | Hazlett et al. | |
| 2003/0050569 A1 | 3/2003 | Shenoy et al. | |
| 2003/0171689 A1 | 9/2003 | Millan et al. | 600/544 |
| 2005/0017870 A1 | 1/2005 | Allison et al. | |
| 2005/0131311 A1 | 6/2005 | Leuthardt et al. | |

FOREIGN PATENT DOCUMENTS

| | | |
|---|---|---|
| EP | 1 164 530 A2 | 12/2001 |
| WO | WO 97/33515 | 9/1997 |
| WO | WO 01/07128 A1 | 2/2001 |
| WO | WO 01/86403 A2 | 11/2001 |
| WO | WO 2004/037086 A1 | 5/2004 |
| WO | WO 20O06/009129 A1 | 1/2006 |

OTHER PUBLICATIONS

Ebrahimi, T. et al., 'Brain-Computer Interface in Multimedia Communication', IEEE Signal Processing Magazine, IEEE Service Center, Piscataway, NJ, US, vol. 20, No. 1, Jan. 2003, pp. 14-24, XP011093777 ISSN: 1053-5888.

Garcia, Gary N. et al., 'Direct Brain-Computer Communication with User Rewarding Mechanism', Proceedings 2003 IEEE International symposium on Information Theory, ISIT 03. Yokohama, Japan, Jun. 29-Jul. 4, 2003, IEEE International Symposium on Information Theory, New York, NY: IEEE, US, Jun. 29, 2003, pp. 221-226, XP010657249 ISBN: 0-7803-7728-1.

Krepki, Roman et al., 'The Berlin Brain-Computer Interface (BBCI) towards a new communication channel for online control of multimedia applications and computer games', $9^{th}$ Proceedings of International Conference on Distributed Multimedia Systems (DMS'03), [Online] 2003, pp. 1-8, XP002463207 Retrieved from the Internet: URL:http://ida.first.fraunhofer.de/bbci> [retrieved on Dec. 17, 2007].

Rani, P., et al., 'Emotion-Sensitive Robots—A New Paradigm for Human-Robot Interaction', Humanoid Robots, 2004 $4^{th}$ IEEE/RAS International Conference on Santa Monica, CA USA Nov. 10-12, 2004, Piscataway, NJ, USA, IEEE, US, vol. 1, Nov. 10, 2004, pp. 149-167, XP010807377 ISBN: 0-7803-8863-1.

* cited by examiner

Component Profile - Horizontal Eye Movement Component

[0.525; 0.462; 1; 0.393; 0.145; 0.526; 0.391; 0.201; 0.084; 0.235; 0.145; 0.107; 0.003; 0.050; 0.040; -0.003; -0.052; -0.054; -0.084; -0.145; -0.215; -0.079; -0.261; -0.379; -0.559; -0.127; -0.490; -0.859; -0.576; -0.679; 0.014; 0.000; -0.006];

Component Profile - Eye-Blink Component

FP1=1;   FP2=1;

F7=0.26;   F3=0.34;   Fz=0.40;   F4=0.39;   F8=0.34;

T7=0.15;   C3=0.24;   Cz=0.26;   C4=0.23;   T8=0.15;

P7=0.07;   P3=0.15;   Pz=0.16;   P4=0.15;   P8=0.09;

O1=0.10;   O2=0.1;

METHOD AND SYSTEM FOR DETECTING AND CLASSIFYING THE MENTAL STATE OF A SUBJECT

FIELD

The present invention relates generally to the detection and classification of the mental state of human subjects. The invention is suitable for use in an electronic entertainment or other platforms in which electroencephalograph (EEG) data is collected and analyzed in order to determine a subject's response to stimuli in real time in order to provide control signals to that platform, and it will be convenient to describe the invention in relation to that exemplary non-limiting application.

Interactions between humans and machines are usually restricted to the use of cumbersome input devices such as keyboards, joysticks and other manually operable controls. Use of such interfaces limits the ability of a use to provide only premeditated and conscious commands.

A number of input devices have been developed to assist disabled users in providing such premeditated and conscious commands. Some of these input devices detect eyeball movement or are voice activated to minimize the physical movement required by a user in order to operate these input devices. Nevertheless, such input devices must be consciously controlled and operated by each user.

A number of studies have been conducted to determine the feasibility of detecting the unconscious behavior or emotional or other mental state of a user. Most of these studies have been conducted in the medical sphere to determine the emotional state or responsiveness of patients to external stimuli in situations where those patients are unable to otherwise communicate with medical staff.

To date though, attempts to detect the emotional state of a subject have been rudimentary only, and are unsuited to use in complex environments, such as contemporary software based gaming or like platforms.

It would be desirable to provide a method and system for detecting and classifying a range of mental states in a manner that was suitable for use in a variety of contemporary applications. It would also be desirable for that system and method to be adaptable to suit a number of applications, without requiring the use of significant data processing resources. It would also be desirable for the method and system for detecting and classifying mental states to be suitable for use in real time applications.

It would also be desirable to provide a method and system for detecting and classifying mental states that ameliorate or overcome one or more disadvantages of known detection and classification methods and systems.

There also exists a need to provide technology that simplifies man machine interactions. It would be preferable for this technology to be robust, powerful and adaptable to a number of platforms and environments. It would also be desirable for technology to optimize the use of natural human interaction techniques so that the man machine interaction is as natural as possible for a human user.

SUMMARY

With that in mind, one aspect of the present invention provides a method of detecting and classifying mental states, including the steps of:

detecting bio-signals from one or more than one bio-signal detector;

transforming the bio-signals into a plurality of different representations;

detecting values of one or more properties of the transformed bio-signal representations; and applying one or more than one mental state detection algorithm to the detected properties in order to classify whether the bio-signals indicate the presence of a predetermined response by a subject.

In a preferred embodiment, the mental state is an emotional state of the subject.

In a preferred embodiment, the step of transforming the bio-signals into a plurality of different representations includes the step of separating the bio-signals into different epochs or time periods.

The step of transforming the bio-signals into a plurality of different representations may further include the step of generating representations of the bio-signal epochs into one or more different domains. For example, each bio-signal epoch may be divided into one or more of different frequency, temporal and spatial domain representations.

The different frequency domain representations may be obtained by dividing each bio-signal epoch into distinguishable frequency bands.

The different temporal domain representations may be obtained by dividing each bio-signal epoch into a plurality of time sequence. In one embodiment, the plurality of time sequence in an epoch may be temporally overlapping.

The different spatial domain representations may be obtained by dividing each bio-signal epoch into a plurality of spatially distinguishable channels. For example, each channel may be derived from a different bio-signal detector. The bio-signal detectors may be scalp electrodes forming part of a headset fitted to the subject.

The different properties of the transformed bio-signal representations to be detected may include the signal power of one or more of the bio-signal representations. The properties may also include signal power of one or more spatially distinguishable channels. The properties may further include a change in the signal power in one or more bio-signal representations. The properties may further include an increase in the signal power of one or more spatially distinguishable channels.

The step of detecting values of one or more properties of the transformed bio-signal representations may also include detecting values of properties between different bio-signal representations. For example, at least the coherence or correlation between bio-signal representations may be detected. The properties of the transformed bio-signal representations to be detected may be the correlation or coherence between signal power in different spatially distinguishable channels. The properties may also include correlation or coherence between changes in signal power in different frequency bands.

The step of applying one or more than one mental state detection algorithm may include:

evaluating the values of detected properties for the bio-signal representation; and comparing results of the evaluation to a signature defining one or more distinctive characteristics of selected properties of the bio-signal representations corresponding to the predetermined response.

The step of applying one or more than one mental state detection algorithm may further include performing dimensional reduction on the number of detected values to derive and minimize a number of state variables for evaluation. The dimensional reduction may be carried out, for example, by performing an analysis of variance (ANOVA) test on the detected values.

The method of comparing results of the evaluation may include comparing the derived state variables to a set of reference state variables corresponding to the signature.

Another aspect of the invention includes a method of calibrating a signature for use in a method of detecting and classifying mental states as described above. The calibration method may include the steps of:

eliciting the predetermined response from the subject;

determining those properties of the bio-signal representations that most significantly indicate the presence of the predetermined response by the subject; and generating the signature of a combination of those properties.

A further aspect of the invention provides an apparatus for detecting and classifying mental states, including:

a sensor interface for receiving bio-signals from one or more than one bio-signal detector; and a processing system for applying one or more than one mental state detection algorithm to representations of the bio-signals in order to classify whether the bio-signals indicate the presence of a predetermined response by a subject.

FIGURES

These and other features, aspects and advantages of the present invention will become better understood with regard to the following description, appended claims, and accompanying figures which depict various views and embodiments of the device, and some of the steps in certain embodiments of the method of the present invention, where:

Figure 1:
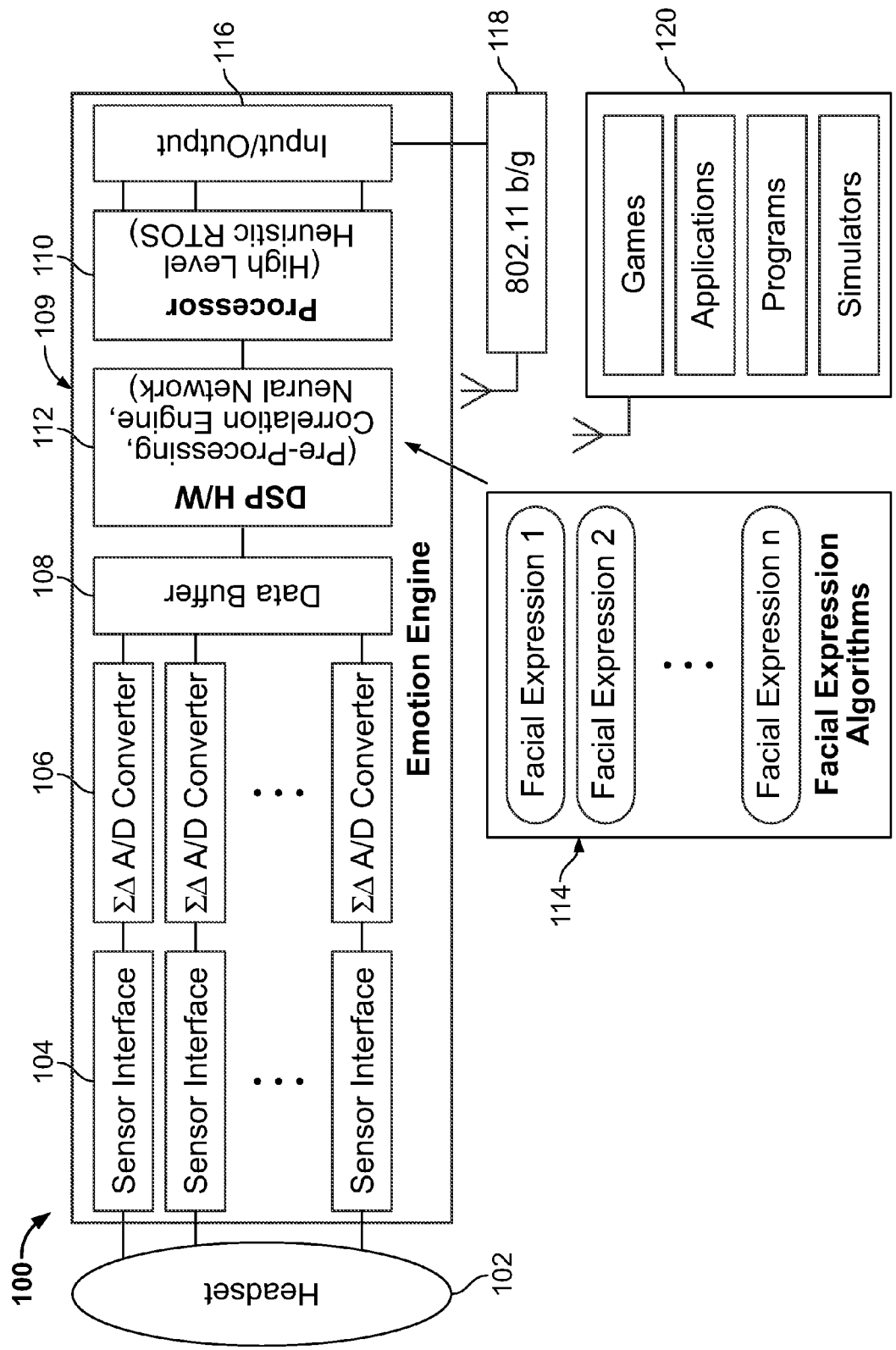
FIG. 1 is a schematic diagram of an apparatus for detecting and classifying mental states in accordance with the present invention.
Figure 4:
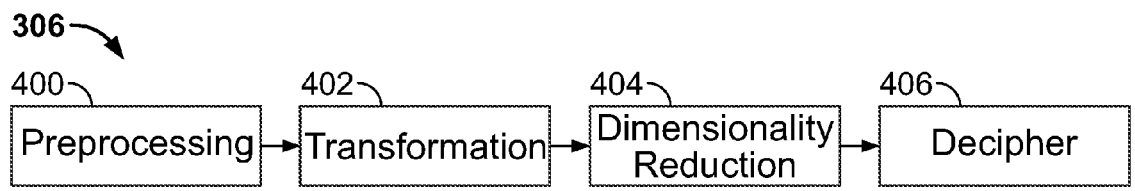
FIG. 4 represents four exemplary processing operations performed during the application of mental state detection algorithms by the apparatus shown in FIG. 1.
Figure 11:
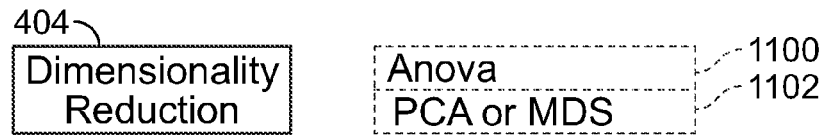
Figure 12:
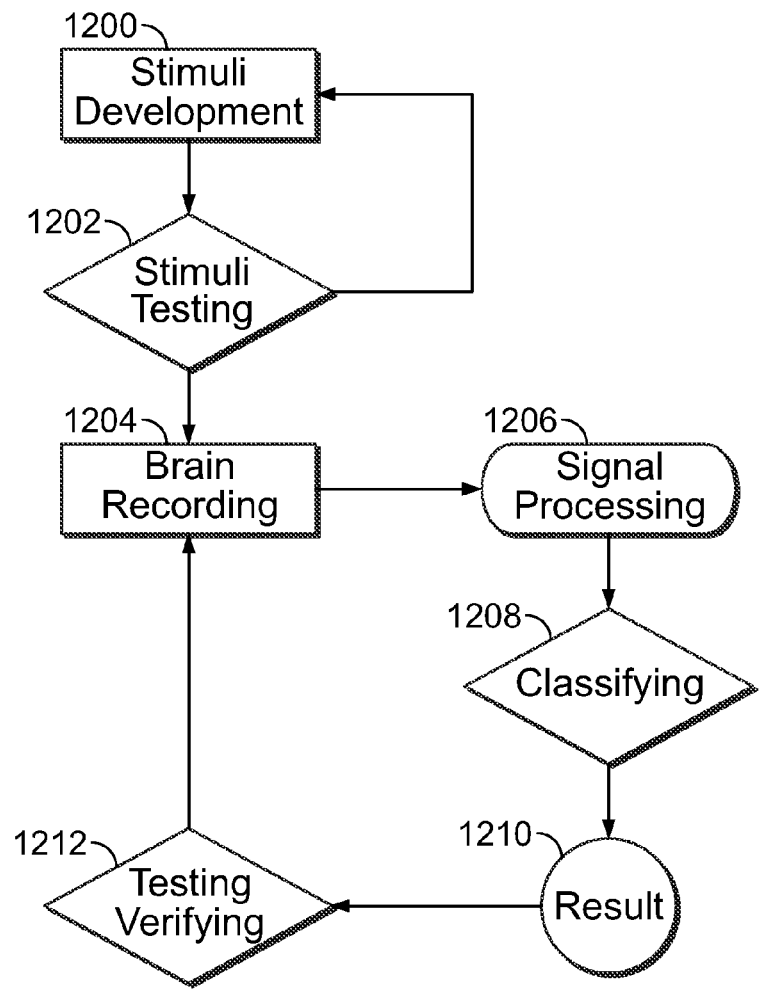
Figure 13:
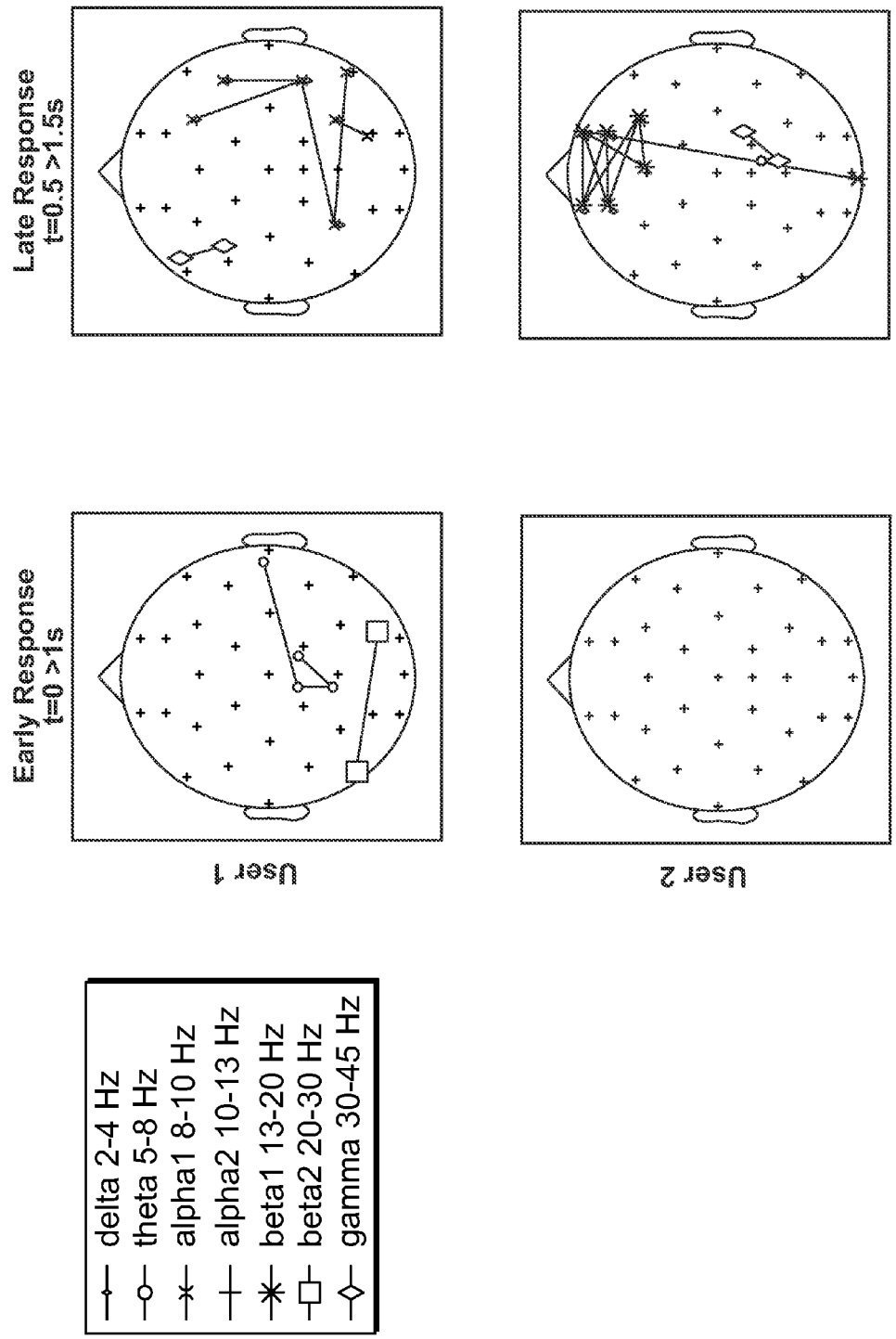

FIG. 11 a schematic diagram showing the steps involved in the dimensional reduction step shown in FIG. 4;

FIG. 12 is a flow chart illustrating exemplary steps performed in the development of signatures defining distinctive characteristics of predefined mental states used in the apparatus of FIG. 1 during the detection and classification of mental states; and FIG. 13 is a diagram shown the positions and frequencies of the ten most significant coherences between channel pairs for two different uses during the development of response signature used by the apparatus shown in FIG. 1 during the detection and classification of emotions.

DESCRIPTION

Turning now to FIG. 1, there is shown an apparatus 100 for detecting and classifying emotions or other mental states. The apparatus 100 includes a head set 102 of bio-signal detectors capable of detecting various bio-signals from a subject, such as electroencephalograph (EEG) signals, electrooculograph (EOG) signals, or like signals. In the exemplary embodiment illustrated in the drawings, the headset 102 includes a series of scalp electrodes for capturing EEG signals from a subject or user. The scalp electrodes may directly contact the scalp or alternately may be of the non-contact type that do not require direct placement on the scalp.

The electrical fluctuations detected over the scalp by the series of scalp sensors are attributed largely to the activity of brain tissue located at or near the scull. The source is the electrical activity of the cerebral cortex, a significant portion of which lies on the outer surface of the brain below the scalp. The scalp electrodes pick up electrical signals naturally produced by the brain and make it possible to observe electrical impulses across the surface of the brain. Although in this exemplary embodiment the headset 102 includes several scalp electrodes, in other embodiments only one or more scalp electrodes may be used in the headset.

Each of the signals detected by the headset 102 of electrodes is fed through a sensor interface 104 and then digitized by the analogue to digital converter 106. Digitized samples of the signal captured by each of the scalp sensors are stored during operation of the apparatus 100 in a data buffer 108 for subsequent processing. The apparatus 100 further includes a processing system 109 including a processing device 110 and associated memory device restoring a series of instructions, otherwise known as a computer program or a computer control logic, to cause the processing device 110 to perform desired functional steps. Notably, the memory device 112 includes a series of instructions to finding one or more than one algorithm 114 for detecting and classifying a predetermined type of emotion. Upon detection of each predefined type of emotion, a corresponding control signal is transmitted to an input/output interface 116 for transmission via a wireless transmission device 118 to a platform 120 for use as a control input by gaming applications, programs, simulators or the like.

In this embodiment, the invention is implemented in software and the series of instructions is stored in the memory device 112. The series of instructions causes the processing device 110 to perform the functions of the invention as described herein. In another embodiment, the invention may be implemented primarily in hardware using, for example, hardware components such as an Application Specific Integrated Circuit (ASIC). Implementation of the hardware state machine so as to perform the functions described herein will be apparent to persons skilled in the relevant art. In yet other embodiments, the invention may be implemented using a combination of both software and hardware.

Figure 2:
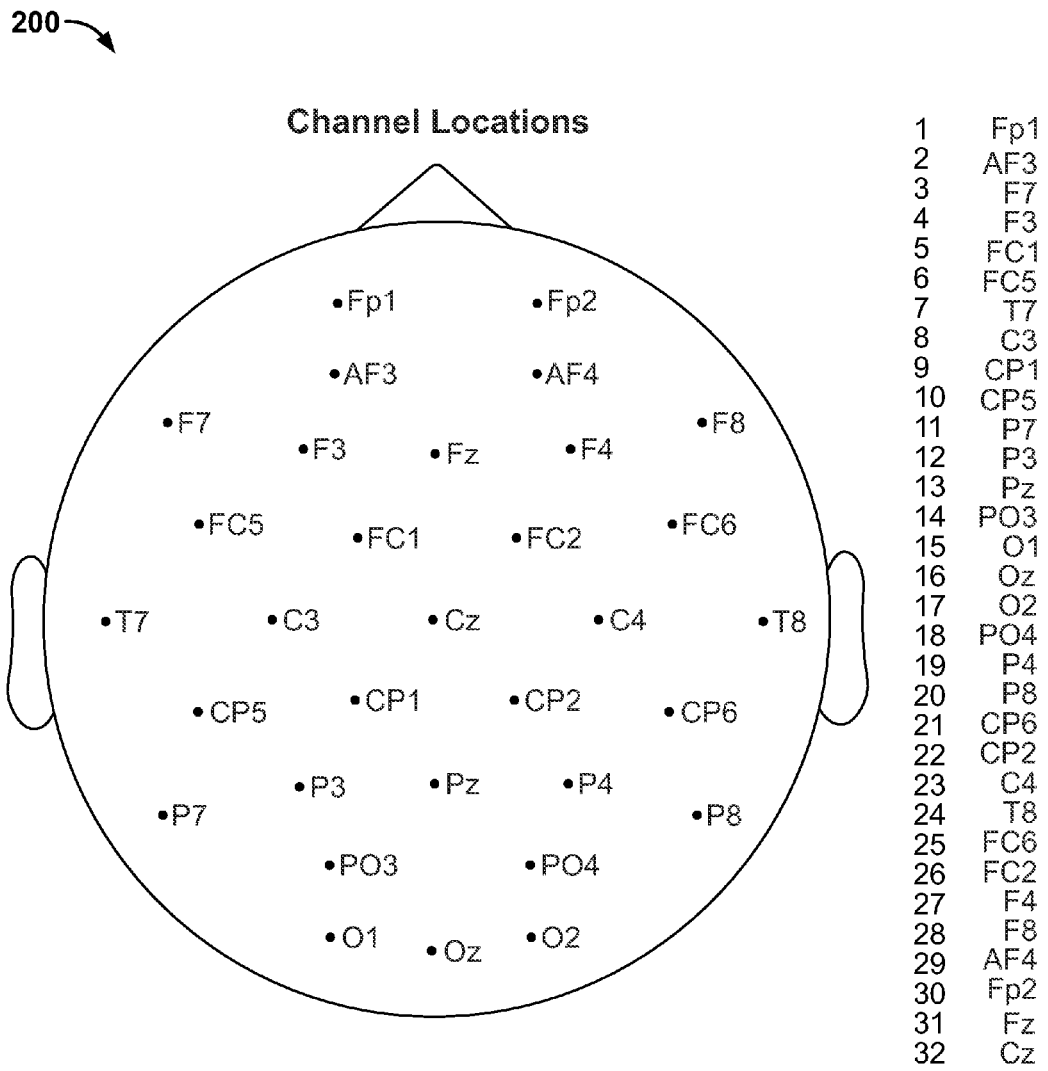
FIG. 2 is a schematic diagram illustrating the position of bio-signal detectors in the form of scalp electrodes forming part of a head set used in the apparatus shown in FIG. 1.

FIG. 2 illustrates one example of a positioning system 200 of the scalp electrodes forming part of the headset 102. The system 200 of electrode placement shown in FIG. 2 is referred to as the "10-20" system and is based on the relationship between the location of an electrode and the underlying area of cerebral cortex. Each point on the electrode placement system 200 indicates a possible scalp electrode position. Each site is indicated by a letter to identify the lobe and a number or other letter to identify the hemisphere location. The letters F, T, C, P, and O stand for Frontal, Temporal, Central, Parietal and Occipital. Even numbers referred to the right hemisphere and odd numbers refer to the left hemisphere. The letter Z refers to an electrode place on the mid-line. The mid-line is a line along the scalp on the sagittal plane originating at the nasion and ending at the inion at the back of the head The "10" and "20" refer to percentages of the mid-line division. The mid-line is divided into 7 positions, namely, Nasion, Fpz, Fz, Cz, Pz, Oz and Inion, and the angular intervals between adjacent positions are 10%, 20%, 20%, 20%, 20% and 10% of the mid-line length respectively.

Figure 3:
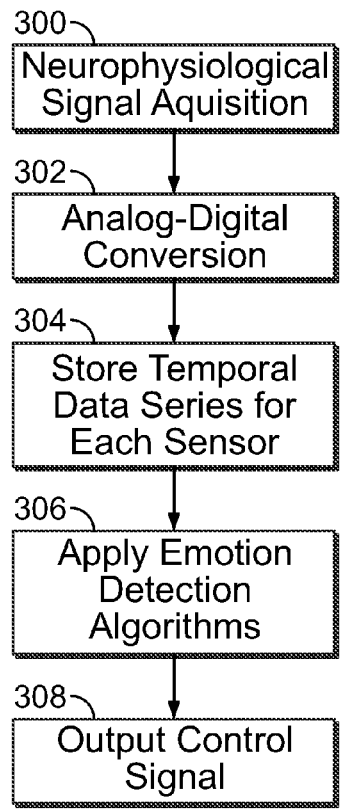
FIG. 3 is a flow chart illustrating the broad functional steps performed during detection and classification of mental states by the apparatus shown in FIG. 1.

As can be seen in FIG. 3, the headset 102, including scalp electrodes positioned according to the system 200, are placed on the head of a subject in order to detect EEG signals. At step 300, the EEG signals are captured by a neurophysiological signal acquisition device and are then Digitized at step 302 using the analogue to digital converters 106. A series of Digitized signals from each of the sensors is then stored at step 304 in the data buffer 108. One or more emotion detection algorithms are then applied at step 306 in order to detect and classify different emotional responses of a subject. Each of the algorithms generates a result representing the emotional response of that subject. These results are then passed to the output block 116 at step 308 where they can be used by a variety of applications. The emotion detection algorithms, in this embodiment, include four processing steps in order to detect emotional responses embedded in the EEG signals. As shown in FIG. 4, these processing steps include a pre-processing step 400, a transformation step 402, a dimensional reduction step 404, and a deciphering step 406. For emotion detection purposes, EEG signals detected by the headset 102 may have a range of characteristics, but for the purposes of illustration typical characteristics are as shown in Table 1 below:

TABLE 1

| Attribute | Value | Unit |
|---|---|---|
| Amplitude | 10-4000 | µV |
| Frequency Range | 0.16-128 | Hz |
| Sampling Rate | 512 | Hz |

The pre-processing stage 400 ensures that the EEG signals are as clear as possible so as to enable the best possible results by the emotion detection algorithms. Possible sources of noise that are desired to be eliminated from the EEG signals include external interference introduced in signal collection, storage and retrieval, as well as intrinsic artefacts that may be present in the EEG signals. For EEG signals, examples of external interference include power line signals at 50/60 Hz and high frequency noise originating from switching circuits residing in the EEG acquisition hardware. The EEG intrinsic artefacts include signal disturbances introduced by facial muscle movements, heartbeats and the like.

Figure 5:
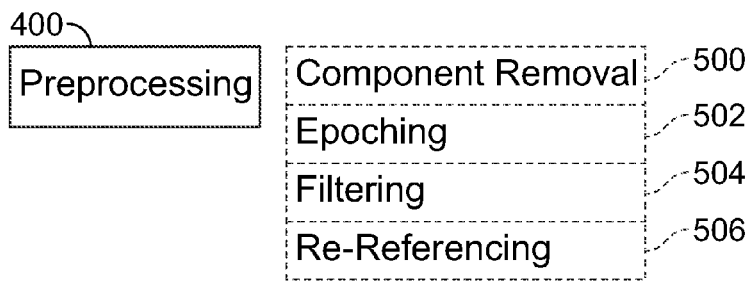
FIG. 5 is a schematic diagram of four exemplary steps performed during the pre-processing step shown in FIG. 4.

As shown in FIG. 5, the pre-processing step 400 includes a component removal step 500, an epoching step 502, a filtering step 504 and a re-referencing step 506. As mentioned above, the purpose of the component removal step 500 is to remove interference components resulting from muscle, eye blink and eye movement artefacts.

EEG consists, in this example, of measurements of the electrical potential at numerous locations on the subject's scalp. Therefore it can be represented as a set of observations $x_n$ of some "signal sources" sm where $n \in [1:N]$, $m \in [1:M]$, n is channel index, N is number of channels, m is source index, M is number of sources. If there exists a set of transfer functions F and G that describe the relationship between $s_m$ and $x_n$, one can then identify with a certain level of confidence which sources or components have a distinct impact on observation $x_n$ and their characteristics.

$$s_m \xrightarrow{F} x_n$$
$$x_n \xrightarrow{G} s_m$$

Different techniques such as Independent Component Analysis (INTERNATIONAL CLASSES) are applied by the apparatus 100 to find components with greatest impact on $x_n$ amplitude often comes from interference such as power line noise, muscle, eyeblink, and eye movement artifacts.

Independent Component Analysis is a linear projection technique in which the transfer function F is found by assuming that the data is a linear combination of a number of unknown sources.

$$x = As + \mu,$$

and the inverse transfer function G is:

$$u = W(x - \mu),$$

where A is the mixing matrix, m is the origin of the data, u is estimation of s, W is the inverse of A, called the unmixing matrix. If m=n, then it is clear that $W = A^{-1}$.

Moreover, ICA also seeks $s_m$ or its estimation u so that u is a set of independent components in statistical sense, i.e., any knowledge about one source implies nothing about the other. Given $s_i$, $s_j \forall I$, $j \in [1:M]$ and $I \neq j$, and p(s) is the probability density function of any given source s, $s_i$ and $s_j$ are said to be independent in statistical sense if and only if $$p(s_i, s_j) = p(s_i) \cdot p(s_j)$$

The ICA algorithm carried out by the apparatus 100 during the component removal in step 500 is implemented in 2 steps:

1) Perform data whitening (or sphering) to remove any correlation in data matrix x.

2) Rotate whitened data recursively in m-dimensional vector space with a goal of minimizing the Gaussianity of data's projection on m-axis.

3) The Gaussianity is derived by the apparatus 100 by measuring the 4th order kurtosis attribute. For a dataset x, kurtosis k is calculated as:

$$k = \frac{\sum (x - \mu)^4}{N \sigma^4} - 3$$

where µ is the mean value, δ is the standard deviation and N is number of data points. The value of k equals zero if the dataset has normal distribution. The data is said to be sub-gaussian or supergaussian for negative and positive k, respectively. Thus, minimizing the Gaussianity of data's projection on m-axis is done by monitoring the sign and modulus of k.

Figure 6:
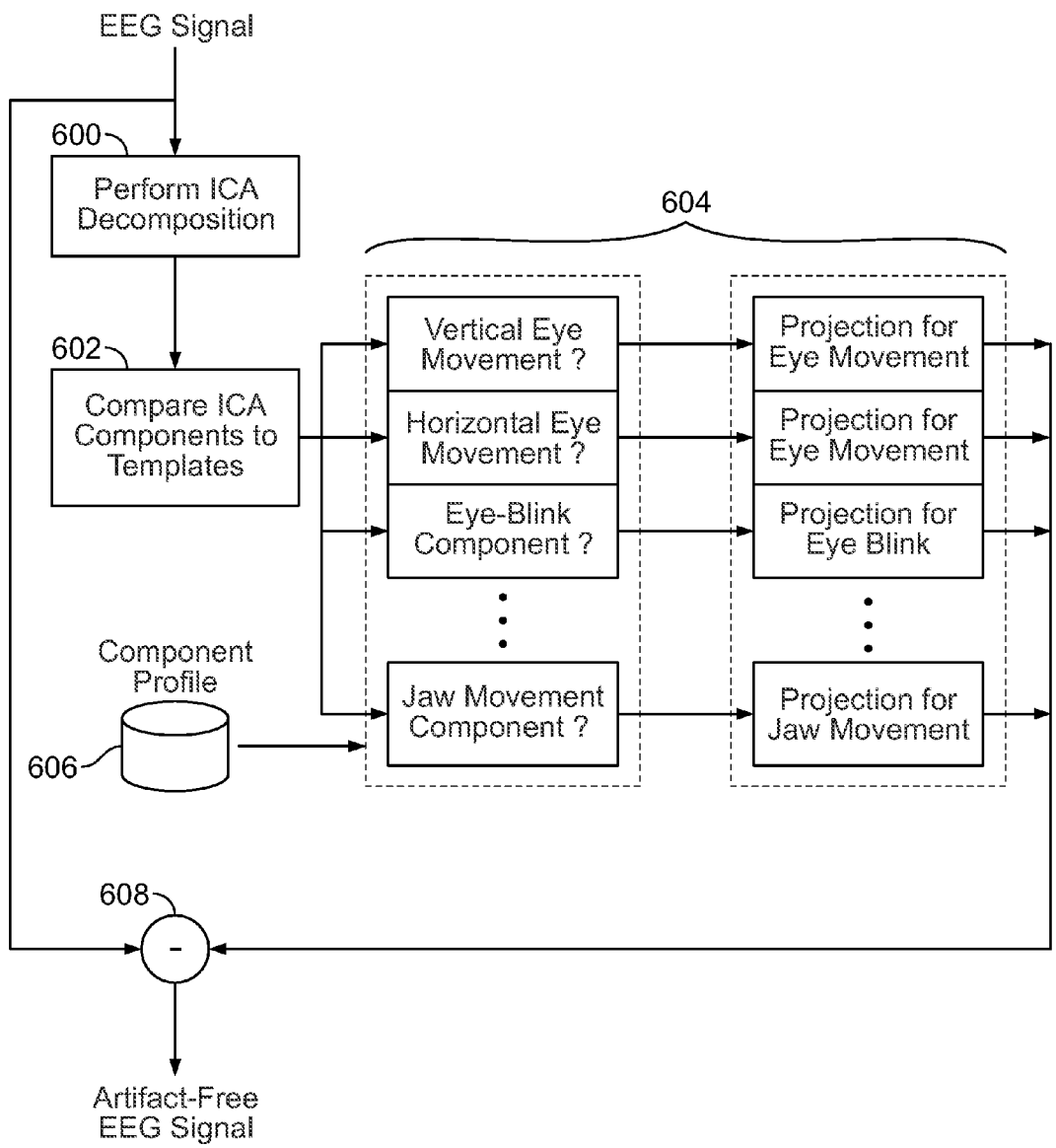
FIG. 6 is a flow chart showing various steps performed by the apparatus 1 during the component removal step forming part of the pre-processing operation shown in FIG. 5.

After applying ICA at step 600 (FIG. 6) on raw EEG data, pattern matching tests are performed by the apparatus 100 at step 602 to see which components correspond to artifacts 604 defined in an artifact profile database 606. If any of these components exist, they are removed by subtracting original EEG signal at step 608 against their projection on all channels.

Figure 7:
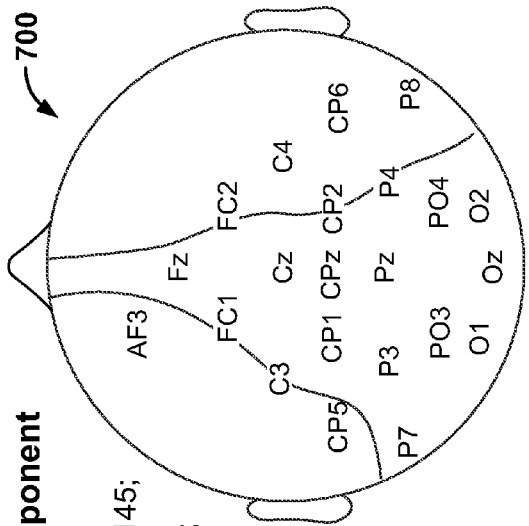
FIGS. 7 and 8 are exemplary component profiles for horizontal eye movement and eye blink components that are intended to be removed by the apparatus shown in FIG. 1 during the component removal step shown in FIG. 6.
Figure 8:
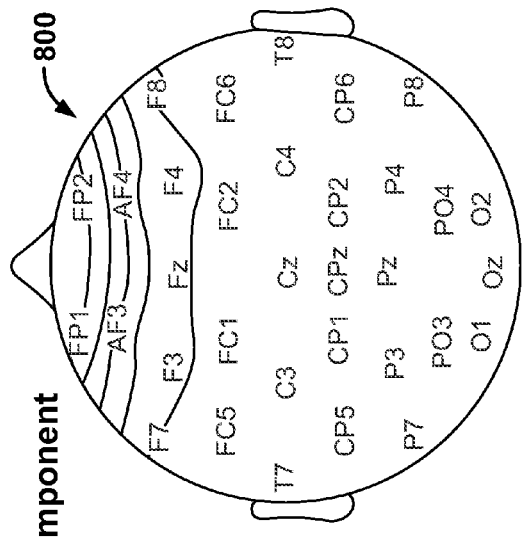

For ICA-based component removal to work effectively, it is important for the processing systems 109 to have enough data points. To generate m stable components, about pm2 data points are desirable where r is in the order of 30~50. FIGS. 7 and 8 show examples of component profiles 700 and 800 respectively for horizontal eye-movement and eye-blink components.

Figure 9:
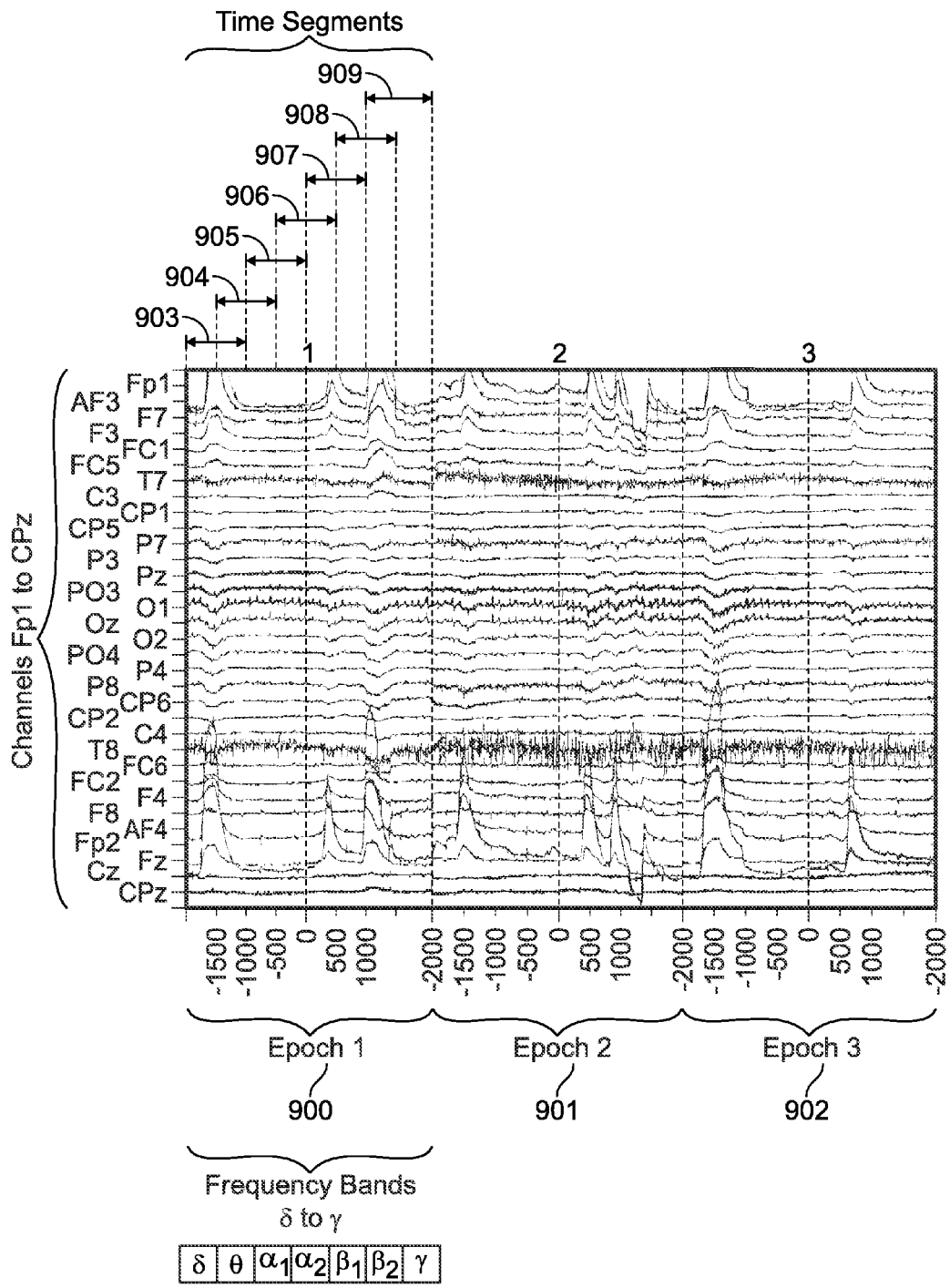
FIG. 9 is a graphical representation of bio-signals processed by the apparatus of FIG. 1 and the transformation of those bio-signals.

In the epoching step 502, the EEG signals are divided into equal length time segments or epochs. Each epoch contains one emotional response signal. In FIG. 9 three epochs 900, 901 and 902 are shown each with 2 seconds before and 2 seconds after the event onset. In general, the baseline before the event is limited to 2 seconds whereas the portion after the event (EEG signal containing emotional response) varies, depending on the current emotion that is being detected.

In the filtering step 504, EEG signals are bandpassed with low and high cutoff frequencies of 0.16 and 128 Hz, respectively. The processing system 109 then acts to divide the EEG signals into various frequency bands. In the exemplary embodiment described herein, seven frequency bands are used with the following frequency ranges: δ(2-4 Hz), θ(4-8 Hz), α1(8-10 Hz), α2(10 13 Hz), β1(13-20 Hz), β2(20-30 Hz) and γ(30-45). In other embodiments of the invention, both the number of and ranges of the frequency bands may be different to the exemplary embodiment.

The referencing step 504 standardizes how the EEG signal is recorded. There are two approaches in the use of reference electrode, originating from the hardware used in the EEG recording. For traditional systems, the signal is measured in a bipolar fashion, i.e., $$s_i = rs_i - rs_f$$

where $s_i$ is recorded signal at channel I $rs_i$ is the voltage (or raw signal) at channel I.

$rs_f$ is the voltage at reference electrode.

An alternative to this system is a monopolar recording in which the recorded signal is the actual signal at electrode site, referenced to a virtual voltage via a feedback loop using Common Mode Signal (CMS) and Driven Right Leg (DRL) electrodes. In bipolar recording, the signal has been already referenced to a common electrode at hardware level whereas in the monopolar case, the obtained signal may be referenced to any real electrode site or combination of sites. Possible approaches for signal referencing are Common Vertex Reference, Average Reference (AR) and Computer Averaged Ear (A1+A2). In our analysis, we adopt Common Vertex Reference using C1 site and Average Reference across all channels.

The apparatus 100 applies one or more than one emotion detection algorithm 114 to a portion of the bio-signals captured by the headset 102 affected by a predefined type of emotional response in order to detect emotions of that predefined type. In order to do so, a mathematical signature defining one or more distinctive characteristics of the predefined type of facial muscle movement is then compared to that mathematical signature. In order to generate the mathematical signature for each emotional response, stimuli are developed at step 1200 shown in FIG. 12 to elicit that particular emotion in the subject. The stimuli are generally in the form of an audio visual presentation or set of commands. The set of stimuli is tested at step 1202 until a high degree of correlation between the developed stimuli and the resultant desired emotional response is obtained. Once a set of effective stimuli is developed, EEG signal recordings are made at step 1204 that contain many examples of the desired emotional response. Once the EEG signal recordings are collected, signal processing operations are performed by the processing system 109 in step 1206 in order to identify one or more distinctive characteristics of each predefined emotion. Identification of these distinctive signal characteristics in each EEG signal recording, as described above, enables classification of the emotional response in a subject to be classified at step 1208 and an output signal representative of the detected type of emotion to be output at step 1210. Testing and verification of the output signal at step 1212 enables a robust data set to be established.

In the transformation stage 402, EEG signals are converted into different representations that facilitate the creation and subsequent detection of emotional signatures so that the emotion detection algorithms 306 can distinguish epochs from different emotions. To do so, the processing system 109 acts to evaluate signal properties in time, frequency and spatial domains. Denote an epoch as where n, I, j, k are epoch, channel, frequency band, and segment index, respectively. Typical values for these parameters are:* i∈[1:32] 32 spatially distinguishable channels (referenced $Fp_1$ to CPz)

j∈[1:7] 7 frequency distinguishable bands (referenced δ to γ)

The processing system 109 divides the epochs 900-902 into time segments. In the example shown in FIG. 9, the epoch 900 is divided into 1 second long segments 903-909 overlapping by half a second. A 3 second long epoch would then yield 5 segments.

Common signal properties to be evaluated by the processing system 109 include the signal power in each channel, the marginal increase in the power in each channel, the correlations/coherence between different channels and the correlations between the marginal changes of the powers in each frequency band. The choice between these properties depends on the types of emotion that are desired to distinguish. In general, marginal properties are more important in case of short term emotional burst whereas in a long term emotion or mood, other properties are more significant.

Figure 10:
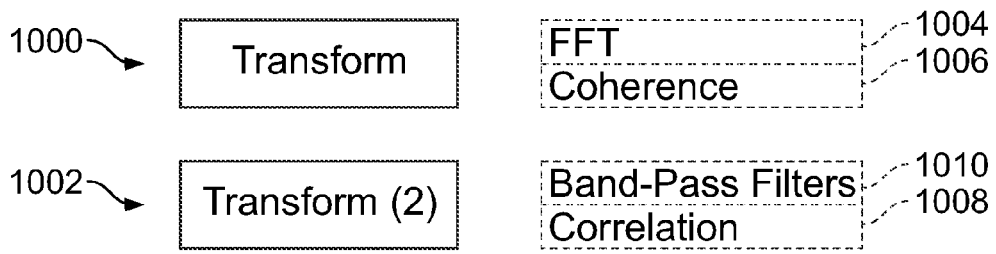
FIG. 10 is a schematic diagram showing two examples of steps carried out by the apparatus 1 during the transformation step shown in FIG. 4.

FIG. 10 shows two possible implementations 1000 and 1002 of the Transform stage in which traditional frequency decomposition techniques (FFT and band-pass filtering) and measures of signal coherence and correlation are adopted by the processing system 109.

The fast Fourier transform (FFT) 1004 is an efficient algorithm of the discrete Fourier transform which reduces the number of computations needed for N data points from $2N_2$ to $2N \log_2 N$. Passing a data channel in time domain through an FFT, one will end up having a description for that data segment in the complex frequency domain.

Coherence is a measure of the amount of association or coupling between two different time series.

Thus, a coherence computation 1006 can be carried out between two channels a and b, in frequency band Cn, where the Fourier components of channels a and b of frequency fμ are xaμ and xbμ is:

Thus, a coherence computation 1006 can be carried out between two channels a and b, in frequency band $\omega_n$, where the Fourier components of channels a and b of frequency $f_\mu$ are $x_{a\mu}$ and $x_{b\mu}$ is:

$$c_{ab\omega_n} = \frac{\sum_{f\mu \in \omega_n} x_{a\mu} x^*_{b\mu}}{\sqrt{\sum_{f\mu \in \omega_n} x^2_{a\mu}} \sqrt{\sum_{f\mu \in \omega_n} x^2_{b\mu}}}$$

Correlation is an alternative to coherence to measure the amount of association or coupling between two different time series. For the same assumption as of coherence section above, a correlation $r_{ab}$, computation 1008 can be carried out between the signals of two channels $x_a(t_i)$ and $x_b(t_i)$, is defined as, $$r_{ab} = \frac{\sum_i (x_{ai} - \bar{x}_a)(x_{bi} - \bar{x}_b)}{\sqrt{\sum_i (x_{ai} - \bar{x}_a)^2 \sum_j (x_{bj} - \bar{x}_b)^2}},$$

where $x_{ai}$ and $x_{bi}$ have already had common band-pass filtering 1010 applied to them.

The operations described in relation to the transformation step 402 often produce a large number of state variables. For example, calculating correlation values for 2 four-second long epochs consisting of 32 channels, using 7 frequency bands gives more than 1 million state variables:

$$^{32}C_2 \times 7^2 \times 7^2 = 1190896$$

Therefore, the Dimensionality reduction (DR) step 404 brings down the number of state variables to a manageable size (~10-100) for the processing system 109 without losing important information. Without the DR stage, the later decipher stage 406 will typically suffer from overfitting data since a large number of samples from each emotional state is usually not available for each subject. FIG. 11 is a schematic diagram showing the steps involved in the dimensional reduction step shown in FIG. 4. In this exemplary embodiment, the processing system 109 uses a combination of ANOVA1 test 1100 and Principal Component Analysis (PCA) 1102 to reduce the imensionality of the state variables.

The ANOVA1 Test 1100 or One way Analysis Of Variance is a statistical test for the heterogeneity of means of 2 or more groups by analysis of the groups' variances. For two observation sets, having normal distribution and unit variances after normalization, the null hypothesis is that they come from the same distribution, i.e., having the same mean μ. After ANOVA1 Test, for each state variable, there is a p-value (from t-test) $p\hat{I}[0,1]$ that indicates the probability that the null hypothesis is correct.

The PCA test 1102, when used for dimensionality reduction purpose, seeks to find a lower dimensional representation, $s = (s_1, \ldots, s_k)^T$ with k<p, of a given p-dimensional random variable $x = (x_1, \ldots, x_p)^T$, that captures as much of the information in the original data as possible, according to some criterion. To achieve this, PCA finds a few orthogonal linear combinations (the principle components (PCs)) of the original variables with the largest variance. The first PC, $s_1$, is the linear combination with the largest variance. We have $s_1 = x^T w_1$, where the p-dimensional coefficient vector $w_1 = (w_{1,1}, \ldots, w_{1,p})^T$ solves:

$$w_1 = \arg\max_{\|w\|=1} \text{Var}\{x^T w\}.$$

The second PC is the linear combination with the second largest variance and orthogonal to the first PC, and so on. Choosing significant state variables from ANOVA1 result (based on small p value), PCA helps further reduce all significant state variables to 10-30 variables which is ready for the decipher stage 406.

The decipher stage 406 takes outputs from PCA step and applies them to a multi layer perceptron neural network to classify whether an epoch contains an emotional response. The processing system 109 uses a standard perceptron with n inputs one hidden layer of m hidden nodes and an output layer with l output nodes. The number of output nodes is determined by how many independent emotions the processing system is trying to recognize. The output vector of the neural network can be expressed as, $$Y = F_2(W_2 \cdot F_1(W_1 \cdot X))$$

where $W_1$ is a m by (n+1) weight matrix; $W_2$ is an l by (m+1) weight matrix (the additional column in the weight matrices allows for a bias term to be added); $X = (X_1, X_2, \ldots X_n)$ is the input vector. $F_1$ and $F_2$ are the activation functions that act on the components of the column vectors separately to produce another column vector and Y is the output vector. The activation function determines how the node is activated by the inputs. The processing system 9 uses a sigmoid function. Other possibilities are a hyperbolic tangent function or even a linear function.

The weight matrices can be determined either recursively or all at once. For the initial training the processing system 109 uses the Levenberg-Marquardt method, although other methods can be used. Once the network has been initially trained, the network weights can be constantly improved using a recursive back-propagation algorithm. In this way, the processing system 109 can account for drift in the emotion signature over time.

For each subject, for the emotion detection algorithms 114 to work optimally, auto-calibration is preferably done since each brain is unique, both physically and functionally. Furthermore, the folding of the cortex of the human brain is highly individual. There is some standardization of the mapping of the neuronal domains across individuals in the bulk of the brain. However, this standardization is not universal and is confounded by, among other things, the handedness of the individual. Moreover, the way in which the external surface of the rain is folded will individualize the potentials detected by EEG regardless of how functionality is mapped in the brain. With this in mind, in order to reliably recognize subtle emotional changes and differentiate between subtly different emotions it is desirable to create individual EEG signatures for each user, hence the auto-calibration phase.

Basically, given a new subject, the aim of an auto-calibration phase is to build a distinct signature for this subject for this particular emotion. In auto-calibration phase, all four stages depicted in FIG. 4 are utilized. Importantly, the dimensionality reduction stage 404 will help automatically identify a set of state variables that will be used to form the signature. The best combination of state variables with associated low p-values that gives good classification on the neural network are chosen for the signature. Between subjects, for the same emotion, the Applicants have found that the state variables set are not the same, but are similar in their distribution across time, frequency and spaces.

After the signature of the emotion is built, the emotion detection algorithm 114 can be used during operation of the apparatus 109 which includes Preprocessing, Transformation and Decipher stages 400-404. Note that the Dimensionality Reduction stage 404 is not required in this operational phase. Once the input data has been transformed during the transformation stage 402, since the set of state variables has been identified during auto-calibration, the processing system 109 can then apply the decipher step 406 on these inputs, giving an emotional response classification result.

One example of the development of a signature will now be described. The user puts on the headset 102. The user then runs training software on the application processor. The training software keeps track of the timing of the emotion evoking events that occur during the game, and communicates with the helmet via a wireless protocol. Different games can be developed to train for a wide variety of emotions.

A particular game was devised in which the subject is shown a playing card and is asked whether the next card will be higher or lower. The bet that the subject will risk is randomly selected from either 10 or 50 points. The correct odds are calculated as to whether the next card will be higher or lower and displayed to the subject, so that the subject understands the amount risked, and the amount that could be potentially won if higher or lower is selected.

After the deal is made the result is displayed and simultaneously a marker is sent to the recorder, so that the epochs can be identified for the calibration step later. After the game has been played for (in this case) about half an hour approximately 250 events had taken place. The epochs are then ranked from the least to the most favorable. The most favorable can be simply ranked by the amount won. The least favorable are selected from all the events in which the user lost 50 pts. Within this group, the events can be ranked inversely to the amount that they would have won. For example, if a 3 was shown to the subject, and the subject selected higher, and lost, this would be ranked as more unfavorable than if a 3 was shown and the user selected lower and lost, as the user knew that this was a high risk choice. In this way a group of epochs can be labeled as containing data from a pleasing event, and another group of epochs that are labeled as containing data from an unpleasant event. There will also be a large group of unlabeled or neutral epochs.

In this embodiment of the invention 32 channels plus a reference channel were used. These were then combined to form 33 signals by taking the median value to be the reference value. The data was then separated into the following 7 sub bands: $\delta$, 2-4 Hz; $\theta$, 4-8 Hz; $\alpha_1$, 8-10 Hz; $\alpha_2$, 10-13 Hz; $\beta_1$, 13-20 Hz; $\beta_2$, 20-30 Hz; and $\gamma$, 30-45 Hz, using FIR band-pass filters. Correlations were then calculated between each channel pair for the 7 different sub bands. This produces $7.^{33}C_2$ (or 3696 variables) for each epoch. In this embodiment, approximately 20 variables are desirable to train the network and this large number of variables is reduced by an analysis of variance test (ANOVA) to determine which variables are statistically the most different in the various reference epochs. If a desired larger number of variables could be extracted from the ANOVA, and this number could be reduced by performing some sort of dimensionality reduction, for example PCA. In this way the variables can be selected from the large number available that together have the most discriminating power.

The data is analyzed in overlapping epochs of one second, where each epoch overlaps its neighbors by half a second. Each event occurs at t=0. Five epochs are considered; two before, two after and one that is centered at t=0. As expected the most significant channel pairs at all frequencies occur in the later two epochs. FIG. 13 shows the positions and frequencies of the 10 most significant coherences between channel pairs for two different users for the two post event epochs. Here it is easy to observe that there are clear differences between users. First, for User 1 the most significant channel pairs occur in both the early and late epochs, whereas the most significant channel pairs for User 2 are all in the later epoch. Second, the significant frequencies and locations are different for each user. User 1 has a lot of $\alpha_1$-band channel pairs on the front and back of the right-hand side of the head. The significant pairs for User 2 are concentrated at the front of the head and the majority of them are in the $b_1$-band.

The game was played by the two users on two different days. Neural networks were trained for both days for both users giving a total of four trained neural networks. Each network was then validated using data from the other day. The results are shown in Table 2.

TABLE 2

Validation scores for each trained network

| Training data | | Validation data |
|---|---|---|
| | User 1 Day 1 | 61% |
| | User 1 Day 2 | 68% |
| | User 2 Day 1 | 77% |
| | User 2 Day 2 | 79% |

A reasonably good classification has been found to be about 60-80%. The classification of the emotions of User 2 is considerably better. This can possibly be explained by the degree of engagement with the game. User 2 reported that she was very engaged, whereas User 1 reported that she was "quite engaged". It is envisaged that more sophisticated games would evoke stronger emotions and produce even better results than those shown in Table 2.

It is to be understood that various modifications and/or additions may be made to the method and system for detecting and classifying the mental state of a subject without departing from the spirit or ambit of the present invention as defined in the claims appended hereto. In particular, whilst the above-described embodiment of the invention has been described in relation to the detection and classification of emotions, it is to be understood that the invention is also applicable to the detection and classification of various other mental states, such as concentration, will, intention to perform predefined actions and the like.

What is claimed is:

1. A method of detecting and classifying mental states, comprising the steps of:
    detecting bio-signals from a bio-signal detector, the bio-signals including at least electroencephalograph (EEG) signals from a subject;
    using a processing device, transforming the electroencephalograph signals into a plurality of different representations, including separating the electroencephalograph signals into different epochs and generating representations of the electroencephalograph signal epochs in a plurality of different frequency domain representations, a plurality of different temporal domain representations and a plurality of different spatial domain representations;
    detecting values of a plurality of different properties of each of the plurality of different frequency domain representations, plurality of different temporal domain representations and plurality of different spatial domain representations; and
    applying a mental state detection algorithm to the detected values of the properties in order to classify whether the electroencephalograph signals indicate the presence of a predetermined mental state of the subject.

2. The method according to claim 1, wherein the different frequency domain representations are obtained by dividing each electroencephalograph signal epoch into distinguishable frequency bands.

3. A method of detecting and classifying mental states, comprising the steps of:
    detecting bio-signals from a bio-signal detector, the bio-signals including at least electroencephalograph (EEG) signals from a subject;
    using a processing device, transforming the electroencephalograph signals into a plurality of different representations, including separating the bio-signals into different epochs, generating representations of the electroencephalograph signal epochs into a plurality of different domains, the different domains including different temporal domain representations, wherein the different temporal domain representations are obtained by dividing each electroencephalograph signal epoch into a plurality of time segments;
    detecting values of properties of the transformed representations; and
    applying one or more than one mental state detection algorithm to the detected values of the properties in order to classify whether the electroencephalograph signals indicate the presence of a predetermined mental state of the subject.

4. The method according to claim 3, wherein the plurality of time segments in each epoch are temporally overlapping.

5. A method of detecting and classifying mental states, comprising the steps of:
    detecting bio-signals from a bio-signal detector, the bio-signals including at least electroencephalograph (EEG) signals from a subject;
    using a processing device, transforming the electroencephalograph signals into a plurality of different representations, including separating the electroencephalograph signals into different epochs, generating representations of the electroencephalograph signal epochs into a plurality of different domains, the different domains including different spatial domain representations, wherein the different spatial domain representations are obtained by dividing each electroencephalograph signal epoch into a plurality of spatially distinguishable channels;
    detecting values of properties of the transformed representations; and
    applying one or more than one mental state detection algorithm to the detected values of the properties in order to classify whether the electroencephalograph signals indicate the presence of a predetermined mental state of the subject.

6. The method according to claim 5, wherein each channel is derived from a different bio-signal detector.

7. The method according to claim 1, wherein the step of detecting values of one or more than one property of the transformed electroencephalograph signal representations comprises detecting values of properties of individual bio-signal representations.

8. The method according to claim 7, wherein one or more than one property comprises signal power of one or more than one electroencephalograph signal representations.

9. The method according to claim 7, wherein one or more than one property comprises signal power of one or more than one spatially distinguishable channels.

10. The method according to claim 7, wherein one or more than one property comprises an increase in signal power of one or more than one electroencephalograph signal representations.

11. The method according to claim 7, wherein one or more than one property comprises increase in signal power of one or more than one spatially distinguishable channels.

12. The method according to claim 1, wherein the step of detecting values of one or more than one property of the transformed electroencephalograph signal representations comprises detecting values of properties between different electroencephalograph signal representations.

13. The method according to claim 12, wherein at least coherence or correlation are detected between different electroencephalograph signal representations.

14. The method according to claim 13, wherein one or more than one property comprises the correlation or coherence between signal power in different spatially distinguishable channels.

15. A method of detecting and classifying mental states, comprising the steps of:
    detecting bio-signals from a bio-signal detector, the bio-signals including at least electroencephalograph (EEG) signals from a subject;
    using a processing device, transforming the electroencephalograph signals into a plurality of different representations,
    detecting values of properties of the transformed representation, including detecting values of properties between different representations, wherein the properties include correlation or coherence between increases in signal power in different frequency bands; and
    applying one or more than one mental state detection algorithm to the detected values of the properties in order to classify whether the electroencephalograph signals indicate the presence of a predetermined mental state of the subject.

16. The method according to claim 1, wherein the mental state is an emotional state of the subject.

17. The method according to claim 1, wherein the step of applying one or more than one mental state detection algorithm comprises:
    evaluating the detected values of the properties of the electroencephalograph signal representations; and
    comparing results of the evaluation to a signature defining a plurality of distinctive characteristics of selected properties of the electroencephalograph signal representations corresponding to the predetermined mental state.

* * * * *